United States Patent
Smeltz et al.

(10) Patent No.: US 7,169,952 B2
(45) Date of Patent: Jan. 30, 2007

(54) PROCESS TO PREPARE SULFONAMIDES

(75) Inventors: Leland A. Smeltz, Langhorne, PA (US); Thomas C. Sedergran, Englishtown, NJ (US); Harold C. Jarrow, Kendall Park, NJ (US)

(73) Assignee: FMC Corporation, Philadelphia, PA (US)

( * ) Notice: Subject to any disclaimer, the term of this patent is extended or adjusted under 35 U.S.C. 154(b) by 785 days.

(21) Appl. No.: 10/296,727

(22) PCT Filed: Jun. 1, 2001

(86) PCT No.: PCT/US01/17931

§ 371 (c)(1),
(2), (4) Date: Jun. 2, 2003

(87) PCT Pub. No.: WO01/94320

PCT Pub. Date: Dec. 13, 2001

(65) Prior Publication Data
US 2003/0236437 A1 Dec. 25, 2003

Related U.S. Application Data

(60) Provisional application No. 60/209,374, filed on Jun. 5, 2000.

(51) Int. Cl.
C07C 303/36 (2006.01)
C07C 303/38 (2006.01)

(52) U.S. Cl. .............................. 564/84; 564/85; 564/86; 564/87; 564/88; 564/89; 564/90; 564/91; 564/92; 564/93; 564/94; 564/95; 564/96; 564/97; 564/98; 564/99

(58) Field of Classification Search .................... None
See application file for complete search history.

(56) References Cited

U.S. PATENT DOCUMENTS

| 4,818,275 A | 4/1989 | Theodoridis |
| 5,990,315 A | 11/1999 | Dumas |

OTHER PUBLICATIONS

Theodoridis, "Synthesis and Chemistry of Agrochemicals III," American Chemical Society (Washington, DC), (1992), p. 134-146.
Marvel, "Identification of Amines. IV. Methanesulfonamides," J. Am. Chem. Soc., No. 51, p. 1272-1274, (1929).
King, "Mechanisms of Hydrolysis and Related Nucleophilic Displacement Reactions of Alkanesulfonyl Chlorides: pH Dependence and the Mechanism of Hydration of Sulfenes," J. Am. Chem. Soc, No. 114, p. 1743-1749, (1992).
Lis and Marisca, "Methanesulfonanilides and the Mannich Reaction," J. Org. Chem., No. 52, p. 4377-4379, (1987).
Han and Cai, "An Efficient and Convenient Synthesis of Formamidines," Tetrahedron Letters, vol. 38 (No. 31), p. 5423-5426, (1997).
Baltas, "Aminolysis of Sulphinamoyl-esters, -sulphonamides and -sulphones. Thiooxamate and thiourea formation via a sulphine intermediate. Thiophilic or carbophilic reaction?," Elsevier Science Publishers (Amsterdam, NL), vol. 52 (No. 47), p. 14865-14876, (Nov. 18, 1996).
Ramon, "Camphorsulphonamide derivatives: a new class of chiral catalysts for the titanium alkoxide-promoted addition of dialkylzinc to aldehydes," Elsevier Science Publshers (Amsterdam, NL), vol. 8 (No. 14), p. 2479-2496, (Jul. 24, 1997).

*Primary Examiner*—Brian Davis
(74) *Attorney, Agent, or Firm*—FMC Corporation

(57) ABSTRACT

A process for the preparation of a sulfonamide of formula (II), comprising reacting at elevated temperature an aniline of formula (I), with a sulfonating agent A of the formula $R^1$—$SO_2$-Z in the presence of a catalytic amount of either: (i) an amide B-1, other than N,N-dimethylformamide, or (ii) a high boiling tertiary amine B-2. Also provided in accordance with the present invention are processes for preparing sulfonamides of formula (II) by reacting an aniline of formula (I) with sulfanating agent A of the formula $R^1$—$SO_2$-Z in the presence of N,N-dimethylformamide, at a temperature in the range of about 120° C. to about 160° C. for about three to about seven hours. X, Y, Z, R and $R^1$ are defined herein

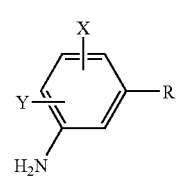

(I)

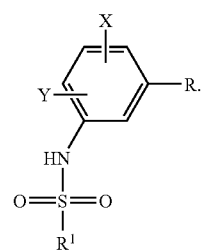

(II)

33 Claims, No Drawings

PROCESS TO PREPARE SULFONAMIDES

RELATED APPLICATIONS

This application claims the benefit of U.S. Provisional Application No. 60/209,374, filed on Jun. 5, 2000.

FIELD OF THE INVENTION

The present invention relates generally to a process for the preparation of sulfonamides. In particular it pertains to preparing N-(substituted phenyl)sulfonamides from the appropriate anilines. More particular, it pertains to the reaction of anilines with a sulfonating agent in the presence of a catalyst to form the N-(substituted phenyl)-sulfonamides.

BACKGROUND OF THE INVENTION

It is known in the art that some N-(substituted phenyl) sulfonamides may be pesticidally active and that such compounds are useful in the preparation of certain pesticides. For example, the use of N-[2,4-dichloro-5-[4-(difluoromethyl)-4,5-dihydro-3-methyl-5-oxo-1H-1,2,4-triazol-1-yl]phenyl]methanesulfonamide as a herbicide is disclosed in U.S. Pat. No. 4,818,275 (issued on Apr. 4, 1989 to FMC Corporation). In U.S. Pat. No. 4,818,275, the N-[2,4-dichloro-5-[4-(difluoromethyl)-4,5-dihydro-3-methyl-5-oxo-1H-1,2,4-triazol-1-yl]phenyl]methanesulfonamide is prepared by first reacting the corresponding arylamine with methanesulfonyl chloride and an excess of triethylamine in methylene chloride and then treating the resulting bis(methanesulfonyl)amino intermediate with sodium hydroxide. In addition, it is also known that N-(substituted aryl)sulfonamides may be prepared directly by treating an arylamine with methanesulfonyl chloride. However, a hydrochloric acid acceptor or scavenger, such as pyridine or triethylamine, must be added in excess to drive the reaction to completion. When large-scale reactions are run, the hydrochloric acid acceptor must be recovered and recycled or disposed of as part of the process. This recovery/recycle or disposal results in significant production costs. Another concern in attempting to convert arylamines to N-(substituted aryl)sulfonamides is low yields of product because of the formation of a bis(methanesulfonylamino) by-product when the reaction is driven to completion. Accordingly, there exists a need to prepare N-(substituted aryl)sulfonamides directly from arylamines without the addition of an acid scavenger and without substantial formation of the bis(methanesulfonylamino) by-product.

SUMMARY OF THE INVENTION

The present invention describes processes for preparing sulfonamides from high concentrations (greater than 50%) of anilines in the presence of a catalyst without the use of acid acceptors and without the substantial formation of bis(methanesulfonylamino) by-products.

The present invention is directed to a process for the preparation of sulfonamides of formula II:

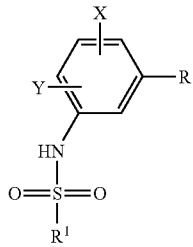

(II)

by reacting at elevated temperature an aniline of formula I:

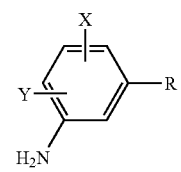

(I)

with a sulfonating agent A of the formula $R^1$—$SO_2$-Z in the presence of a catalytic amount of either (i) an amide B-1 or (ii) a high boiling tertiary amine B-2, in which X, Y, Z, R, and $R^1$ are defined below.

Also provided in accordance with the present invention are processes for preparing sulfonamides of formula II by reacting an aniline of formula I with sulfonating agent A of the formula $R^1$—$SO_2$-Z in the presence of N,N-dimethylformamide, at a temperature in the range of about 120° C. to about 160° C. for about three to about seven hours.

DETAILED DESCRIPTION OF THE INVENTION

In one embodiment of the present invention, a process is provided for the preparation of a sulfonamide of formula II:

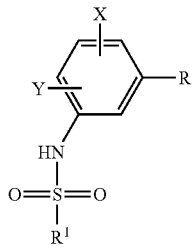

(II)

which process comprises reacting at elevated temperature an aniline of formula I:

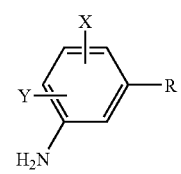

(I)

with a suitable sulfonating agent A of the formula $R^1$—$SO_2$-Z in the presence of a catalytic amount of (i) an amide B-1, other than N,N-dimethylformamide, or (ii) a high-boiling tertiary amine B-2;

wherein:

X and Y in both formulae I and II and Z are each independently selected from the group consisting of hydrogen, halo, alkyl, haloalkyl, amino, nitro, alkoxy, hydroxy, anhydridyl, alkylthio, arylthio, aryloxy, alkylsulfonyl, arylsulfonyl, and substituted or unsubstituted aryl, the substituents comprising one or more members selected from the group consisting of halo, $C_{1-20}$ alkyl, $C_{1-20}$ alkoxy, nitro, amino, amido, alkylthio, aryl, arylthio, aryloxy, alkylsulfonyl, and arylsulfonyl;

R in both formulae I and II is selected from the group consisting of hydrogen, alkyl, haloalkyl, aryloxy, substituted or unsubstituted aryl, and substituted or unsubstituted heterocyclyl, the substituents comprising one or more members selected from the group consisting of halo, $C_{1-20}$ alkyl, $C_{1-20}$ alkoxy, nitro, amino, amido, alkylthio, aryl, arylthio, aryloxy, alkylsulfonyl, and arylsulfonyl; and, $R^1$ is selected from the group consisting of hydrogen, alkyl, haloalkyl, and aryl.

Preferred sulfonamides prepared by the present invention are those in which X and Y are halo; R is a substituted or unsubstituted heterocyclyl, the substituents comprising one or more members selected from the group consisting of halo, $C_{1-20}$ alkyl, $C_{1-20}$ alkoxy, nitro, amino, amido, alkylthio, aryloxy, aryl, arylthio, alkylsulfonyl, and arylsulfonyl; and $R^1$ is aryl or alkyl.

Particularly preferred sulfonamides prepared by the present invention are those in which X and Y are chloro or fluoro; R is 4-difluoromethyl-4,5-dihydro-3-methyl-5-oxo-1H-1,2,4-triazol-1-yl, 1-methyl-6-trifluoromethyl-2,4-(1H,3H)-pyrimidinedion-3-yl, or 1-amino-6-trifluoromethyl-2,4-(1H,3H)-pyrimidinedion-3-yl; and $R^1$ is methyl. An even more preferred sulfonamide prepared by the present invention is that in which X is 2-chloro or 2-fluoro, Y is 4-chloro, R is 4-difluoromethyl-4,5-dihydro-3-methyl-5-oxo-1H-1,2,4-triazol-1-yl, and $R^1$ is methyl.

Preferred anilines that can be used in the present invention are those in which X and Y are halo and R is a substituted or unsubstituted heterocyclyl, the substituents comprising one or more members selected from the group consisting of halo, $C_{1-20}$ alkyl, $C_{1-20}$ alkoxy, nitro, amino, amido, alkylthio, aryloxy, aryl, arylthio, alkylsulfonyl, and arylsulfonyl.

Particularly preferred anilines that can be used in the present invention are those in which X and Y are chloro or fluoro and R is 4-difluoromethyl-4,5-dihydro-3-methyl-5-oxo-1H-1,2,4triazol-1-yl, 1-methyl-6-trifluoromethyl-2,4-(1H,3H)-pyrimidinedion-3-yl, or 1-amino-6-trifluoromethyl-2,4-(1H,3H)-pyrimidinedion-3-yl. An even more preferred aniline that can be used in the present invention is that in which X is 2-chloro or 2-fluoro, Y is 4-chloro, and R is 4-difluoromethyl-4,5-dihydro-3-methyl-5-oxo-1H-1,2,4-triazol-1-yl. Suitable sulfonating agents A that may used in the present invention are those substances that allow for the attachment of a sulfonyl moiety on an amino group. Examples of sulfonating agents A that may used in the present invention include, but are not limited to, those having the formula $R^1$—$SO_2$-Z, wherein $R^1$ and Z are as defined above. Preferred sulfonating agents A that can be used in the present invention include those agents of the formula $R^1$—$SO_2$-Z in which $R^1$ is aryl or alkyl and Z is halo or anhydridyl. Particularly preferred sulfonating A include those agents of the formula $R^1$—$SO_2$-Z in which $R^1$ is alkyl and Z is halo. An even more preferred sulfonating agent A is an agent of the formula $R^1$—$SO_2$-Z in which $R^1$ is methyl and Z is chloro. "Catalytic amount" as utilized herein shall mean an amount of either amide B-1 or high boiling tertiary amine B-2 that when added to a reaction will cause the reaction to proceed at a faster rate but in which said amide B-1 or high boiling tertiary amine B-2 does not undergo any permanent chemical change.

Suitable amides B-1 and high boiling tertiary amines B-2 that may be used in the present invention are those amides or amines that have the ability to form an activated complex with the aniline of formula I. Examples of amides B-1 or amines B-2 that can be used in the present invention include, but are not limited to, pyrrolidinones, ureas, acetamides, phosphoramides, isoquinolines, and triazolones. Preferred amides B-1 or amines B-2 that can used in the present invention are 1-methyl-2-pyrrolidinone (hereafter referred to as NMP), 1,1,3,3-tetramethylurea, N,N-dimethylacetamide (hereafter referred to as DMAC), hexamethylphosphoramide (hereafter referred to as HMPA), isoquinoline, and 1-(2,4-dichloro-5-acetamidophenyl)-4-difluoromethyl-4,5-dihydro-3-methyl-1H-1,2,4-triazol-5-one (hereafter referred to as 5-N-acetyl).

The reaction is preferably carried out at elevated temperature, such as from about 110° C. to about 160° C., more preferably from about 120° C. to about 150° C., preferably for about three to about 12 hours, more preferably for about three to about seven hours. The reaction can be run at lower temperatures, but generally will require an appreciably longer time to complete. In addition, the reaction may be run at atmospheric or increased pressure.

The reaction may be carried out by combining the aniline I with about 1 to about 5, preferably about 1.3 to about 4, molar equivalents of sulfonating agent A to one molar equivalent of aniline I and a catalytic amount, for example, about 0.001 to about 1, preferably about 0.001 to about 0.06, molar equivalents of amide B-1 or high boiling tertiary amine B-2 to one molar equivalent of aniline I.

In addition, the reaction may be carried out neat or in a solvent. Suitable solvents that can be used in the present invention are those that allow for the formation of a miscible mixture with the aniline of formula I at elevated temperature. Examples of solvents that may be used in the present invention include, but are not limited to, aromatic, alkane, or alkene solvents. Preferred solvents that can be used in the present invention are toluene, xylene, and diethylbenzene. A particularly preferred solvent that can be used in the present invention is toluene.

In another embodiment of the invention, the sulfonamide of formula II, where X, Y, R and $R^1$ are as defined above, is prepared by reacting the desired aniline of formula I with a sulfonating agent A of the formula $R^1$—$SO_2$-Z, where $R^1$ and Z are as defined above, and N,N-dimethylformamide (hereafter referred to as DMF) for about three to about seven hours, preferably about four to about seven hours, at about 120° C. to about 160° C., preferably about 125° C. to about 150° C.

When using DMF, the reaction may be carried out at a sulfonating agent A to aniline I ratio of about 1.5 to about 6, preferably about 1.5 to about 4, molar equivalents of sulfonating agent A to one molar equivalent of aniline I, and at a DMF to aniline I ratio of about 0.001 to about 0.09, preferably about 0.001 to about 0.05, molar equivalents of DMF to one molar equivalent of aniline I. The sulfonating agents A disclosed above may also be used in conjunction with DMF. A preferred sulfonating agent A that may be used in conjunction with DMF is one in which $R^1$ is methyl and Z is chloro.

Similar to above, the reaction utilizing DMF may be carried out at atmospheric or increased pressure. In addition, the reaction with DMF may be carried out neat or in a suitable solvent. The solvents disclosed above may also be used in conjunction with DMF. Preferred solvents that may be used in conjunction with DMF are toluene, xylene, and diethylbenzene.

The preferred and particularly preferred sulfonamides of formula II and/or anilines of formula I disclosed above may also be prepared and/or used in conjunction with DMF.

The processes of the present invention are safer and more cost efficient than existing methods because they do not use a hydrochloric acid acceptor, the catalysts used are safer, and the time needed to complete the reaction is reduced. In addition to these advantages, the processes of the present invention generally convert in excess of 90%, often in excess of 95%, of the starting aniline material to the sulfonamides II.

As used in this specification and unless otherwise indicated the substituent terms "alkyl", "alkoxy", "aryloxy", and "alkoxyarylamino", used alone or as part of a larger moiety, include straight or branched chains of at least one or two carbon atoms, as appropriate to the substituent, and preferably up to 20 carbon atoms, more preferably up to ten carbon atoms, most preferably up to seven carbon atoms. "Halogen" or "halo" refers to fluorine, bromine, iodine, or chlorine. "Aryl" refers to an aromatic ring structure having 5 to 10 carbon atoms. "Heteroaryl" refers to an aromatic ring structure having 1 to 4 nitrogen, sulfur, or oxygen atoms or a combination thereof as hetero ring components, with the balance being carbon atoms. "High boiling" refers to a compound having a boiling point above 140° C. at ambient pressure. The term "ambient temperature" as utilized herein shall mean a temperature not exceeding 30° C. The term "elevated temperature" as utilized herein shall mean a temperature above ambient temperature, for example, a temperature in the range of about 110° C. to about 160° C.

The present invention is now described in more detail by reference to the following examples, but it should be understood that the invention is not construed as being limited thereto.

EXAMPLE 1

This example illustrates one protocol for the preparation of N-[2,4-dichloro-5-[4-(difluoromethyl)-4,5-dihydro-3-methyl-5-oxo-1H-1,2,4-triazol-1-yl]phenyl]methane-sulfonamide using NMP as the catalyst.

Under a nitrogen atmosphere, a stirred solution of 20.0 grams (0.054 mole—1.0 equiv.) of 83.1% pure 1-(5-amino-2,4-dichlorophenyl)-4,5-dihydro-4-difluoromethyl-3-methyl-1,2,4-triazol-5(1H)-one, 9.2 grams (0.08 mole—1.5 equiv.) of methanesulfonyl chloride, 0.17 gram (0.002 mole—0.04 equiv.) of NMP, and 17 grams of toluene (% wt/wt. triazol-5(1H)-one to solvent—118%) was heated at 110° C. for six hours.

EXAMPLE 2

This example illustrates one protocol for the preparation of N-[2,4-dichloro-5-[4-(difluoromethyl)-4,5-dihydro-3-methyl-5-oxo-1H-1,2,4-triazol-1-yl]phenyl]methane-sulfonamide using DMF as the catalyst.

To a one liter roundbottom flask equipped with a mechanical stirrer and a thermometer was added 104.5 grams (0.3 mole—1.0 equiv.) of 88.7% pure 1-(5-amino-2,4-dichlorophenyl)-4,5-dihydro-4-difluoromethyl-3-methyl-1,2,4-triazol-5(1H)-one, 52.6 grams (0.45 mole—1.5 equiv.) of methanesulfonyl chloride, 0.9 gram (0.012 mole—0.04 equiv.) of DMF, and 93 grams of toluene (% wt/wt. triazol-5(1H)-one to solvent—112%). Upon completion of addition, the reaction mixture was heated at about 148° C. for four hours. After this time, the reaction mixture was cooled to 95° C. and an additional 569 grams of toluene (% wt/wt. triazol-5(1H)-one to total solvent—15.8%) was added. Upon completion of addition, the reaction mixture was allowed to cool to ambient temperature and then stirred for about 18 hours. After this time, the reaction mixture was heated to 60° C. and then transferred to a second one-liter roundbottom flask equipped with a mechanical stirrer and a thermometer. Once the transfer was complete, the solution was heated to 85° C. and 490 mL of warm (85° C.) water were added. The resulting mixture was heated to 85° C. and stirred for 30 minutes. After this time, the organic layer was separated from the aqueous layer and an additional 490 mL of warm (85° C.) water was added. The resulting mixture was again heated to 85° C. and stirred for an additional 30 minutes. The organic layer was separated from the aqueous layer and allowed to cool to ambient temperature, and then stirred for about 48 hours. After this time, the reaction mixture was heated to 90° C. to effect dissolution and then cooled to 85° C. and stirred for 30 minutes. After this time, the reaction mixture was cooled to 20° C. during an eight hour period at a rate of 5° C./hour drop in temperature for the first four hours and then at a rate of 10° C./hour for the last four hours. In order to facilitate crystallization, about one (1) gram (about 1 wt %) of technical N-[2,4-dichloro-5-[4-(difluoromethyl)-4,5-diyhdro-3-methyl-5-oxo-1H-1,2,4-triazol-1-yl]phenyl]methane-sulfonamide was added at 70–75° C. during the eight hour cool down period. Once at the appropriate temperature, the organic layer was transferred into an appropriate centrifuge, where it was spun for 30 minutes to remove the mother liquor. The filter cake was washed with three 50 mL portions of cold toluene charged directly into the centrifuge. The mixture was spun for 30 minutes to remove the toluene wash. The filter cake was removed from the centrifuge and dried at 65° C./30 mm Hg for four hours, yielding 108.99 grams (85%) of 90.5% pure N-[2,4-dichloro-5-[4-(difluoromethyl)-4,5-dihydro-3-methyl-5-oxo-1H-1,2,4-triazol-1-yl]phenyl]methanesulfonamide.

EXAMPLE 3

This example illustrates one protocol for the preparation of N-[2,4-dichloro-5-[4-(difluoromethyl)-4,5-dihydro-3-methyl-5-oxo-1H-1,2,4-triazol-1-yl]phenyl]methane-sulfonamide using 1,1,3,3-tetramethylurea as the catalyst.

Under a nitrogen atmosphere, a stirred solution of 20.0 grams (0.054 mole—1.0 equiv.) of 83.1% pure 1-(5-amino-2,4-dichlorophenyl)-4,5-dihydro-4-difluoromethyl-3-methyl-1,2,4-triazol-5(1H)-one, 9.2 grams (0.08 mole—1.5 equiv.) of methanesulfonyl chloride, 0.17 gram (0.001 mole—0.03 equiv.) of 1,1,3,3-tetramethylurea, and 17 grams of xylene (% wt/wt. triazol-5(1H)-one to solvent—118%) was heated at 141° C. to 144° C. for six hours. After this time, gas chromatography (GC) analysis indicated 1.2% of the 1,2,4-triazol-5(1H)-one starting material remaining.

EXAMPLE 4

This example illustrates one protocol for the preparation of N-[2,4-dichloro-5-[4-(difluoromethyl)-4,5-dihydro-3-methyl-5-oxo-1H-1,2,4-triazol-1-yl]-methane-sulfonamide using DMF as the catalyst.

Under a nitrogen atmosphere, a stirred solution of 20.0 grams (0.054 mole—1.0 equiv.) of 83.1% pure 1-(5-amino-2,4-dichlorophenyl)-4,5-dihydro-4-difluoromethyl-3-methyl-1,2,4-triazol-5(1H)-one, 17 grams of xylene (% wt/wt. triazol-5(1H)-one to solvent—118%), 9.2 grams (0.08 mole—1.5 equiv.) of methanesulfonyl chloride, and 0.17 gram (0.002 mole—0.04 equiv.) of DMF was heated at 140° C. for four hours. After this time, GC analysis of the reaction mixture indicated 99.4% conversion of the 1,2,4-triazol-5 (1H)-one starting material. The reaction mixture was then cooled to 23° C. and stored for later use.

EXAMPLE 5

This example illustrates one protocol for the preparation of N-[2,4-dichloro-5-[4-(difluoromethyl)-4,5-dihydro-3-methyl-5-oxo-1H-1,2,4-triazol-1-yl]phenyl]-methane-sulfonamide using DMAC as the catalyst.

To a 500 mL roundbottom flask equipped with a mechanical stirrer and a thermometer was added 20.0 grams (0.05 mole—1.0 equiv.) of 79.0% pure 1-(5-amino-2,4-dichlorophenyl)-4,5-dihydro-4-difluoromethyl-3-methyl-1,2,4-triazol-5(1H)-one, 0.2 gram (0.002 mole—0.04 equiv.) of DMAC, 19.0 grams (0.16 mole—3.2 equiv.) of methanesulfonyl chloride, and 19 grams of toluene (% wt/wt. triazol-5(1H)-one to solvent—105%). Upon completion of addition, the reaction mixture was heated to 119–120° C. and then stirred for about 6.75 hours. After this time, GC analysis of the reaction mixture indicated the complete conversion of the 1,2,4-triazol-5(1H)-one starting material.

EXAMPLE 6

This example illustrates one protocol for the preparation of N-[2,4-dichloro-5-[4-(difluoromethyl)-4,5-dihydro-3-methyl-5-oxo-1H-1,2,4-triazol-1-yl]phenyl]-methane-sulfonamide using HMPA as the catalyst.

Under a nitrogen atmosphere, a stirred solution of 10.0 grams (0.029 mole—1.0 equiv.) of 88.7% pure 1-(5-amino-2,4-dichlorophenyl)-4,5-dihydro-4-difluoromethyl-3-methyl-1,2,4-triazol-5(1H)-one, 8.9 grams of xylene (% wt/wt. triazol-5(1H)-one to solvent—112%), 4.9 grams (0.043 mole—1.5 equiv.) of methanesulfonyl chloride, and 0.1 gram (0.0006 mole—0.02 equiv.) of HMPA was heated at 148° C. for 4.5 hours. After this time, GC analysis of the reaction mixture indicated 98% conversion of the 1,2,4-triazol-5(1H)-one starting material.

EXAMPLE 7

This example illustrates one protocol for the preparation of N-[2,4-dichloro-5-[4-(difluoromethyl)-4,5-dihydro-3-methyl-5-oxo-1H-1,2,4-triazol-1-yl]phenyl]-methane-sulfonamide using 5-N-acetyl as the catalyst.

To a 500 mL roundbottom flask equipped with a mechanical stirrer and thermometer was added 20.0 grams (0.065 mole—1.0 equiv.) of 1-(5-amino-2,4-dichlorophenyl)-4,5-dihydro-4-difluoromethyl-3-methyl-1,2,4-triazol-5(1H)-one, 19.0 grams of xylene (% wt/wt. triazol-5(1H)-one to solvent—105%), 11.0 grams (0.096 mole—1.5 equiv.) of methane-sulfonyl chloride, and 1.6 grams (0.005 mole—0.08 equiv.) of 5-N-acetyl. Upon completion of addition, the reaction mixture was heated to 145° C. where it stirred for 4.67 hours. After this time, GC analysis of the reaction mixture indicated 99.6% conversion of the 1,2,4-triazol-5 (1H)-one starting material.

EXAMPLE 8

This example illustrates one protocol for the preparation of N-[2,4-dichloro-5-[4-(difluoromethyl)-4,5-dihydro-3-methyl-5-oxo-1H-1,2,4-triazol-1-yl]phenyl]-methane-sulfonamide using DMF as the catalyst. (50 Gallon Pilot Plant Scale)

Under a nitrogen atmosphere, a 50 gallon glass lined reactor was charged with 262 pounds of a 16 wt % 1-(5-amino-2,4-dichlorophenyl)-4,5-dihydro-4-difluoromethyl-3-methyl-1,2,4-triazol-5(1H)-one in toluene solution. The solution was stirred and heated to about 105–115° C. During the heating-up period, the nitrogen atmosphere was discontinued and the reaction vessel was sealed under a vacuum of about 750–780 mm Hg. Once at the prescribed temperature, the toluene was removed at a rate to maintain the reaction temperature at about 110–120° C. and the reaction vessel pressure at 750–780 mm Hg, yielding 78 pounds of a 50 wt % solution of 1-(5-amino-2,4-dichlorophenyl)-4,5dihydro-4-difluoromethyl-3-methyl-1,2,4-triazol-5(1H)-one (0.126 lb-mole; 1.0 equiv.—17.69 Kg) in toluene. The reaction vessel was cooled to about 85–92° C. and 168 grams (0.005 lb-moles; 0.04 equiv.—0.37 pound) of DMF was added. Methanesulfonyl chloride, 23.7 pounds (0.207 lb-mole; 1.64 equiv.—10.75 Kg), was added at a rate to maintain the reaction mixture temperature between 85–92° C. The reaction mixture temperature was then slowly brought to 140–145° C. while the reaction vessel pressure was maintained at 14–17 psig, at a rate of about 10° C. per hour. During the heating to 140–145° C., any hydrogen chloride gas that evolved was vented off. The reaction mixture was then stirred at 140–145° C. for eight hours. During the eight-hour heating period, the reaction mixture was analyzed by GC every hour to determine the conversion of starting material to product. After the eight-hour heating period, an acceptable 99% conversion of starting material to product had been achieved. The reaction vessel was then cooled to about 83–87° C. and then vented to atmospheric pressure during a 15-minute period. Once at atmospheric pressure, 230 pounds of fresh toluene was added. The resulting solution was stirred for 30 minutes and then transferred to a separate 50 gallon glass lined reactor that had been previously charged with 275–285 pounds of water and heated to 80–83° C. The resulting mixture was stirred at 80–83° C. for 25–35 minutes and then allowed to settle for about 25–35 minutes. The organic layer was separated from the aqueous layer and an additional 275–285 pounds of water was added. After a repeat of the previously described stirring and settling, the organic layer was separated from the aqueous layer and then cooled to 20° C. during an eight hour period at a rate of 5° C./hour for the first four hours and then at a rate of 10° C./hour for the last four hours. In order to facilitate crystallization, 0.5 pound of technical N-[2,4-dichloro-5-[4-(difluoromethyl)-4,5-dihydro-3-methyl-5-oxo-1H-1,2,4-triazol-1-yl]phenyl]-methanesulfonamide was added at 70–75° C. during the eight hour cool down period. Once at the end temperature, the organic layer was transferred into an appropriate centrifuge, where it was spun for 30 minutes to remove the mother liquor. The mother liquor was charged back into the reaction vessel, where it was stirred for 10 minutes to remove any remaining product. The mother liquor was then transferred into the centrifuge, where it was spun as previously described. The filter cake was washed with 50 pounds of fresh toluene charged directly into the centrifuge. The mixture was spun for 30 minutes to remove the toluene wash. The mother liquor and toluene wash were collected in the same receiver for reclamation of any dissolved product. The filter cake was removed from the centrifuge and dried at 80° C./30 mm Hg for eight hours, yielding 55 pounds of N-[2,4-dichloro-5-[4-(difluoromethyl)-4,5-dihydro-3-methyl-5-oxo-1H-1,2,4-triazol-1-yl] phenyl]methane-sulfonamide.

EXAMPLE 9

This example illustrates one protocol for the preparation of N-[2-chloro-4-fluoro-5-[1-methyl-6-trifluoromethyl-2,4-(1H,3H)-pyrimidinedion-3-yl]phenyl]methanesulfonamide using NMP as the catalyst.

To a stirred solution of 37.5 grams (0.1 mole—1.0 equiv.) of 3-(5-amino-4-chloro-2-flurophenyl)-1-methyl-6-trifluoromethyl-2,4-(1H,3H)-pyrimidinedione in 37.5 grams of xylene (% wt/wt. pyrimidinedione to solvent—100%) is added 17.4 grams (0.15 mole—1.5 equiv.) of methanesulfonyl chloride followed by 0.17 gram (0.002 mole—0.04 equiv.) of NMP. Upon completion of addition, the reaction mixture is heated at about 115° C. for six hours.

While the invention has been described in detail and with reference to specific embodiments thereof, it will be apparent to one skilled in the art that various changes and modifications can be made therein without departing from the spirit and scope thereof.

We claim:

1. A process for the preparation of a sulfonamide of formula II:

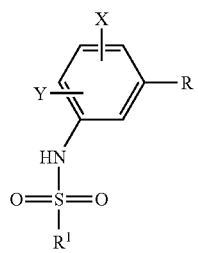

comprising reacting at elevated temperature at least the following: (1) an aniline of formula I:

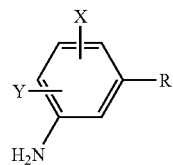

with (2) a sulfonating agent A of the formula $R^1$—$SO_2$-Z in the presence of (3) a catalytic amount of: (i) an amide B-1 or (ii) a high boiling tertiary amine B-2;

wherein:

B-1 is other than N,N-dimethylformamide;

X and Y in both formulae I and II and Z are each independently selected from the group consisting of hydrogen, halo, alkyl, haloalkyl, amino, nitro, alkoxy, hydroxy, anhydridyl, alkylthio, arylthio, aryloxy, alkylsulfonyl, arylsulfonyl, and substituted or unsubstituted aryl, the substituents of said substituted aryl comprising one or more members selected from the group consisting of halo, $C_{1-20}$ alkyl, $C_{1-20}$ alkoxy, nitro, amino, amido, alkylthio, aryl, arylthio, aryloxy, alkylsulfonyl, and arylsulfonyl;

R in both formulae I and II is selected from the group consisting of hydrogen, alkyl, haloalkyl, aryloxy, substituted or unsubstituted aryl and substituted or unsubstituted heterocyclyl, the substituents of said substituted aryl or heterocyclyl comprising one or more members selected from the group consisting of halo, $C_{1-20}$ alkyl, $C_{1-20}$ alkoxy, nitro, amino, amido, alkylthio, aryl, arylthio, aryloxy, alkylsulfonyl, and arylsulfonyl; and, $R^1$ is selected from the group consisting of hydrogen, alkyl, haloalkyl, and aryl.

2. The process of claim 1, wherein X and Y are each halo.

3. The process of claim 1, wherein X is 2-chloro or 2-fluoro and Y is 4-chloro.

4. The process of claim 1, wherein R is a substituted or unsubstituted heterocyclyl, the substituents comprising one or more members selected from the group consisting of halo, $C_{1-20}$ alkyl, $C_{1-20}$ alkoxy, nitro, amino, amido, alkylthio, aryl, arylthio, aryloxy, alkylsulfonyl, and arylsulfonyl.

5. The process of claim 4, wherein R is 4-difluoromethyl-4,5-dihydro-3-methyl-5-oxo-1H-1,2,4-triazol-1-yl, 1-methyl-6-trifluoromethyl-2,4-(1H,3H)-pyrimidinedion-3-yl, or 1-amino-6-trifluoromethyl-2,4-(1H,3H)-pyrimidinedion-3-yl.

6. The process of claim 1, wherein $R^1$ is aryl or alkyl and Z is halo or anhydridyl.

7. The process of claim 6, wherein $R^1$ is methyl and Z is chloro.

8. The process of claim 1, wherein X is 2-chloro; Y is 4-chloro; R is 4-difluoromethyl-4,5-dihydro-3-methyl-5-oxo-1H-1,2,4-triazol-1-yl; and $R^1$ is methyl.

9. The process of claim 1, wherein the amide B-1 and tertiary amine B-2 are independently selected from the group consisting of 1-methyl-2-pyrrolidinone, 1,1,3,3-tetramethylurea, N,N-dimethylacetamide, hexamethylphosphoramide, isoquinoline, and 1-(2,4-dichloro-5-acetamidophenyl)-4-difluoromethyl-4,5-dihydro-3-methyl-1H-1,2,4-triazol-5-one.

10. The process of claim 1, wherein the reaction is carried out in a solvent.

11. The process of claim 10, wherein the solvent is an aromatic, alkane, or alkene solvent.

12. The process of claim 11, wherein the solvent is selected from the group consisting of toluene, xylene, and diethylbenzene.

13. The process of claim 12, wherein the solvent is toluene.

14. The process of claim 1, wherein the reaction mixture is heated at about 110° C. to about 160° C. for about three to about 12 hours.

15. The process of claim 14, wherein the reaction mixture is heated at about 120° C. to about 150° C. for about three to about seven hours.

16. The process of claim 1, wherein about 1 to about 5 molar equivalents of sulfonating agent A are present per one molar equivalent of aniline I.

17. The process of claim 16, wherein about 1.3 to about 4 molar equivalents of sulfonating agent A are present per one molar equivalent of aniline I.

18. A process for the preparation of a sulfonamide of formula II:

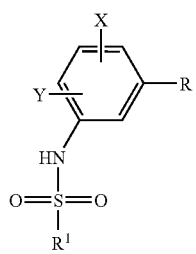

which comprises reacting (1) an aniline of formula I:

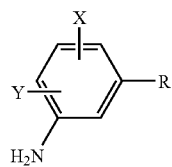

with (2) sulfonating agent A of the formula $R^1$—$SO_2$-Z in the presence of (3) N,N-dimethylformamide, at a temperature in the range of about 120° C. to about 160° C. for about three to about seven hours;

wherein:

X and Y in both formulae I and II and Z are each independently selected from hydrogen, halo, alkyl, haloalkyl, amino, nitro, alkoxy, hydroxy, anhydridyl, alkylthio, arylthio, aryloxy, alkylsulfonyl, arylsulfonyl, and substituted or unsubstituted aryl, the substituents of said substituted aryl comprising one or more members selected from the group consisting of halo, $C_{1-20}$ alkyl, $C_{1-20}$ alkoxy, nitro, amino, amido, alkylthio, aryl, arylthio, aryloxy, alkylsulfonyl, and arylsulfonyl;

R in both formulae I and II is selected from the group consisting of hydrogen, alkyl, haloalkyl, aryloxy, substituted or unsubstituted aryl and substituted or unsubstituted heterocyclyl, the substituents of said substituted aryl or heterocyclyl comprising one or more members selected from the group consisting of halo, $C_{1-20}$ alkyl, $C_{1-20}$ alkoxy, nitro, amino, amido, alkylthio, aryl, arylthio, aryloxy, alkylsulfonyl, and arylsulfonyl; and, $R^1$ is selected from the group consisting of hydrogen alkyl, haloalkyl, and aryl.

19. The process of claim 18, wherein X and Y are each halo.

20. The process of claim 19, wherein X is 2-chloro or 2-fluoro and Y is 4-chloro.

21. The process of claim 18, wherein R is a substituted or unsubstituted heterocyclyl, the substituents comprising one or more members selected from the group consisting of halo, $C_{1-20}$ alkyl, $C_{1-20}$ alkoxy, nitro, amino, amido, alkylthio, aryloxy, aryl, arylthio, alkylsulfonyl, and arylsulfonyl.

22. The process of claim 21, wherein R is 4-difluoromethyl-4,5-dihydro-3-methyl-5-oxo-1H-1,2,4-triazol-1-yl, 1-methyl-6-trifluoromethyl-2,4-(1H,3H)-pyrimidinedion-3-yl, or 1-amino-6-trifluoromethyl-2,4-(1H,3H)-pyrimidinedion-3-yl.

23. The process of claim 18, wherein $R^1$ is alkyl and Z is halo.

24. The process of claim 23, wherein $R^1$ is methyl and Z is chloro.

25. The process of claim 18, wherein X is 2-chloro; Y is 4-chloro; R is 4-difluoromethyl-4,5-dihydro-3-methyl-5-oxo-1H-1,2,4-triazol-1-yl; and $R^1$ is methyl.

26. The process of claim 18, wherein the reaction is carried out in a solvent.

27. The process of claim 26, wherein the solvent is an aromatic, alkane, or alkene solvent.

28. The process of claim 27, wherein the solvent is selected from the group consisting of toluene, xylene, and diethylbenzene.

29. The process of claim 18, wherein the reaction mixture is heated at about 125° C. to about 150° C. for about four to about seven hours.

30. The process of claim 18, wherein about 1.5 to about 6 molar equivalents of sulfonating agent A are present per one molar equivalent of aniline I.

31. The process of claim 30, wherein about 1.5 to about 4 molar equivalents of sulfonating agent A are present per one molar equivalent of aniline I.

32. The process of claim 18, wherein about 0.001 to about 0.09 molar equivalent of N,N-dimethylformamide is present per one molar equivalent of aniline I.

33. The process of claim 32, wherein about 0.001 to about 0.05 molar equivalent of N,N-dimethylformamide is present per one molar equivalent of aniline I.

* * * * *